US00PP32355P2

(12) United States Plant Patent
van Zoest

(10) Patent No.: US PP32,355 P2
(45) Date of Patent: Oct. 20, 2020

(54) ***CLEMATIS* PLANT NAMED 'ZO14100'**

(50) Latin Name: ***Clematis* hybrid**
Varietal Denomination: Zo14100

(71) Applicant: J. van Zoest Beheer B.V., Boskoop (NL)

(72) Inventor: Jan van Zoest, Boskoop (NL)

(73) Assignee: J. VAN ZOEST BEHEER B.V., Boskoop (NL)

( * ) Notice: Subject to any disclaimer, the term of this patent is extended or adjusted under 35 U.S.C. 154(b) by 0 days.

(21) Appl. No.: 16/602,079

(22) Filed: Aug. 1, 2019

(30) Foreign Application Priority Data

Mar. 18, 2019 (QZ) ..... PBR 2019/0728

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./226, 228
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of hybrid *Clematis* plant named 'Zo14100' that is characterized by its dwarf plant habit, its non-climbing plant habit, its very floriferous blooming habit, its yellow flowers, and its cold hardiness at least to U.S.D.A. Zone 5.

2 Drawing Sheets

Botanical classification: *Clematis* hybrid.
Variety denomination: 'Zo14100'.

CROSS REFERENCE TO A RELATED APPLICATION

This application claims priority to European Community Plant Variety Office (CPVO) Plant Breeder's Rights Application No. 2019/0728 filed on Mar. 18, 2019, the entire contents of which is incorporated by reference herein.

BACKGROUND OF THE INVENTION

The present invention relates to a new and distinct cultivar of *Clematis* of hybrid origin and will be referred to hereafter by its cultivar name 'Zo14100'. 'Zo14100' is a herbaceous perennial grown for use as a landscape plant.

The Inventor discovered the new cultivar in August of 2014 as a naturally occurring whole plant mutation of *Clematis* 'Tangutica' (not patented, used in the trade as a cultivar even though it is also the species name) in a seedling block at a nursery in Boskoop, The Netherlands. The seedling block had been sown with seed collected from numerous seedling plants of *Clematis* 'Tangutica', therefore the exact parent plant is unknown.

Asexual propagation of the new cultivar was first accomplished by softwood stem cuttings under the direction of the Inventor in Boskoop, The Netherlands in 2015. Asexual propagation by softwood stem cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish *Clematis* 'Zo14100' as a unique cultivar of *Clematis*.

1. 'Zo14100' exhibits a dwarf plant habit.
2. 'Zo14100' exhibits a non-climbing habit.
3. 'Zo14100' exhibits a very floriferous blooming habit.
4. 'Zo14100' exhibits cold hardiness at least to U.S.D.A. Zone 5.

The potential parent plants of 'Zo14100' all differ from 'Zo14100' in having a climbing plant habits and in being less floriferous. 'Zo14100' can be most closely compared to the *Clematis* cultivars 'Kugotia' (U.S. Plant Pat. No. 10,952) and 'Bill MacKenzie' (not patented). Both are similar to 'Zo14100' in having yellow color flowers and in cold hardiness. Both differ from 'Zo14100' in being taller in height with a climbing habit and in having flowers that are larger in size with dark purple stamen connectives.

STATEMENT DESIGNATING A GRACE PERIOD UNDER 102(B)(1)

The Applicant claims prior art exemption under 35 U.S.C. 102(b)(1) for disclosure and/or sales prior to the filing date but less than one year prior to the effective filing date if need be. Information about the claimed plant was obtained from a direct or indirect disclosure from the Inventor; including but not limited to disclosures on websites by J Van Zoest, Plantarium, Plantipp, Thompson and Morgan, Taylors *Clematis*, Brushwood Nursery, and Waitrose Garden.

BRIEF DESCRIPTION OF THE DRAWINGS

The accompanying colored photographs illustrate the overall appearance and distinct characteristics of the new *Clematis*. The photographs were taken of a two-year-old plant as grown outdoors in a 2-liter rose container in Boskoop, The Netherlands.

The photograph in FIG. 1 provides a view of 'Zo14100' in bloom.

Figure 1:
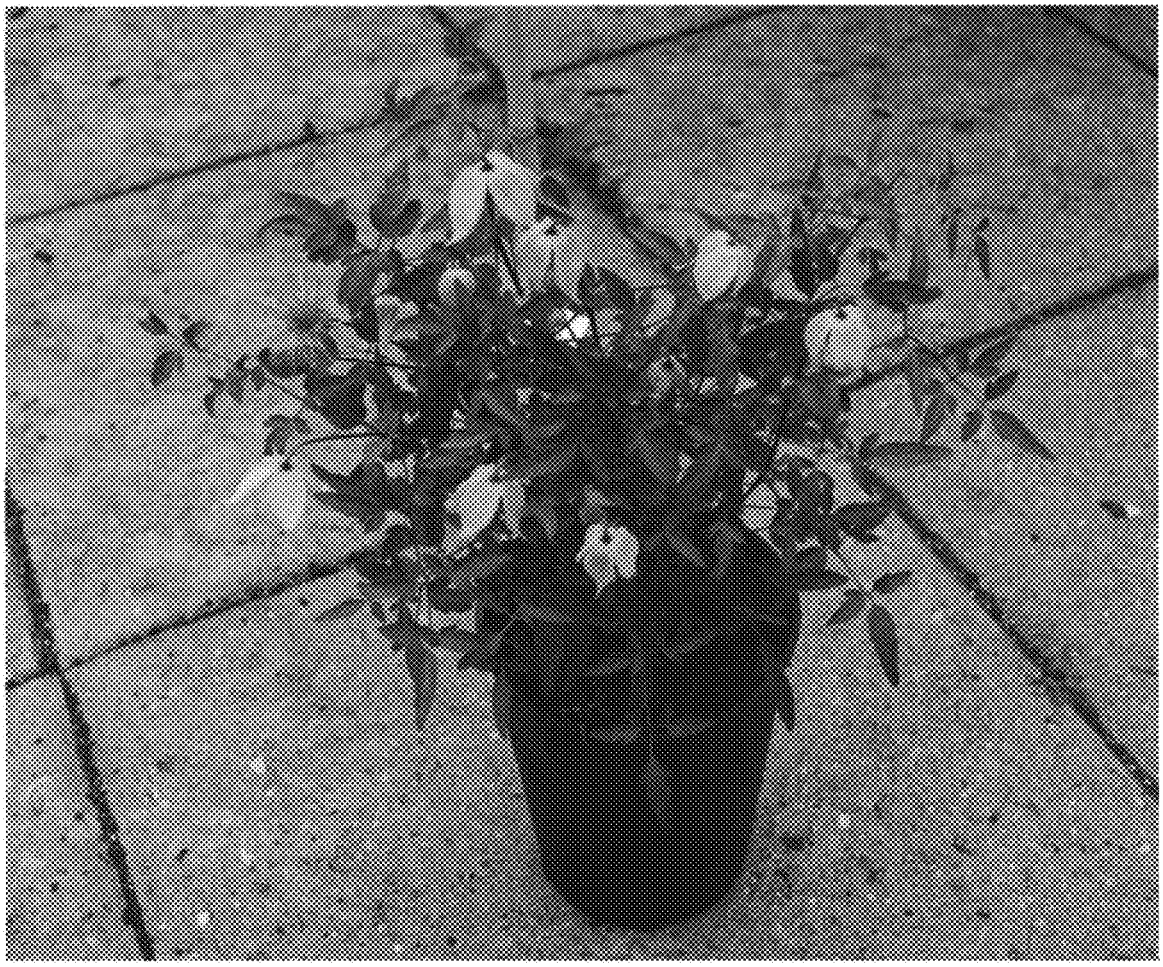
Figure 2:
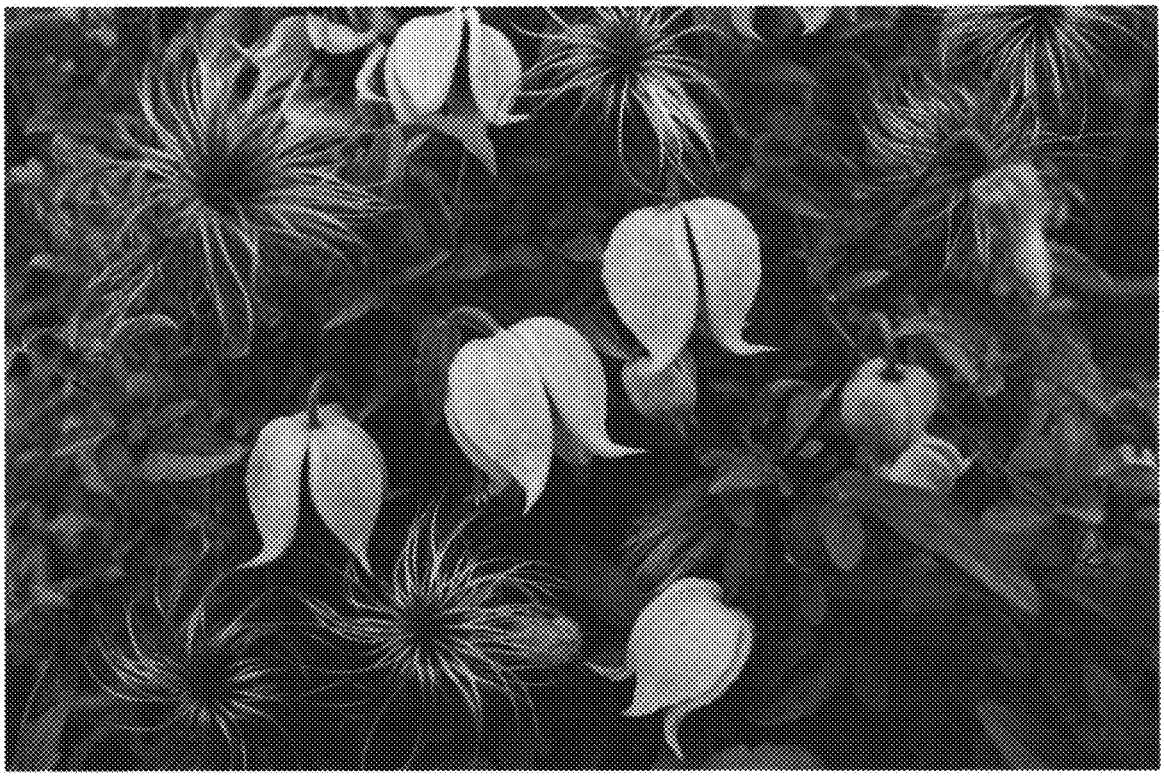

The photograph in FIG. 2 provides a close-up view of the flowers and seed heads of 'Zo14100'.

Figure 3:
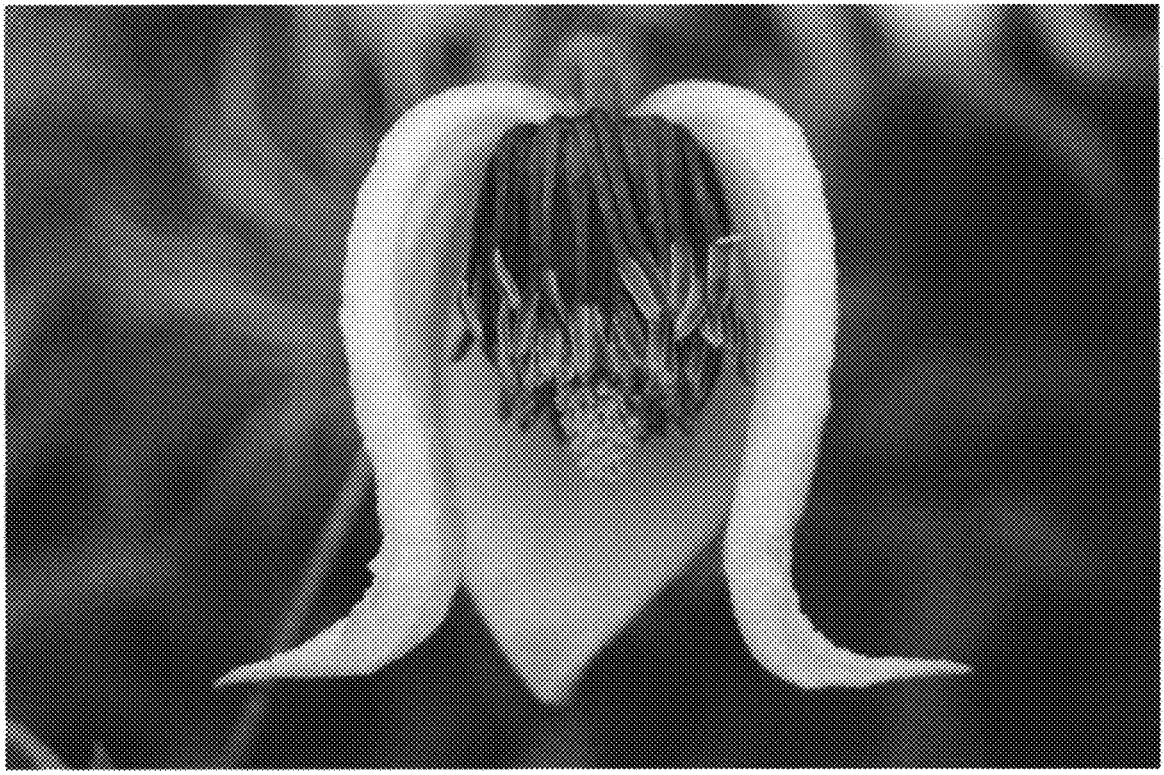

The photograph in FIG. 3 provides a close-up view of a cross section of a flower of 'Zo14100'.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of two-year-old plants as grown outdoors in 2-Liter rose containers in Boskoop, The Netherlands. The phenotype of the new cultivar may vary with variations in environmental, climatic and cultural conditions, as the cultivar has not been tested under all possible environmental conditions. The color determination is in accordance with The 2015 Colour Chart of The Royal Horticultural Society, London, England, except where general color terms of ordinary dictionary significance are used.

General description:

*Blooming period*.—End of May into September in The Netherlands.

*Plant type*.—Deciduous, blooms on new shoots only.

*Plant habit*.—Non-climbing, bushy habit.

*Height and spread*.—A three-year-old plant reaches an average of 40 cm in height (with an occasional shoot reaching up to 60 cm) and 50 cm in diameter.

*Cold hardiness*.—At least to U.S.D.A. Zone 5.

*Diseases and pests*.—No disease or pest problems have been observed, however no susceptibility or resistance to specific causative agents have been identified.

*Root description*.—Fibrous, 164B to 164C in color.

*Propagation*.—Softwood stem cuttings.

*Time required for root initiation*.—Roots develop in 4 weeks in summer under greenhouse conditions.

*Time required for root development*.—60 to 75 days to fully develop a 7 cm container from a 5 cm cutting.

*Growth rate*.—Moderate.

Stem description:

*Shape*.—Round with 6 ribbed angles.

*Stem color*.—143C, flushed with N77A.

*Stem size*.—Up to 20 cm in length when the terminal flower appears, sometimes a shoot up to 60 cm, an average of 2 mm in width.

*Stem surface*.—Young; densely pubescent, mature; sparsely pubescent covered with short hairs.

*Internode length*.—Up to 12 cm.

*Strength*.—Strong and flexible, cracks at a 45° angle.

*Branching*.—From the base.

Foliage description:

*Leaf arrangement*.—Opposite.

*Leaf division*.—Simple to ternate.

*Leaf size*.—Up to 18 cm in length and 10 cm in width.

*Leaf attachment*.—Petiolate.

*Leaf fragrance*.—Sharp fragrance when crushed.

*Leaflet shape*.—Side leaflets; ovate, terminal leaflets; lanceolate.

*Leaflet size*.—Side leaflets; up to 4 cm in length and 1.3 cm in width, terminal leaflets; up to 5 cm in length and 1.5 cm in width.

*Leaflet base*.—Side leaflets; obtuse to cordate, terminal leaflets; obtuse to cuneate.

*Leaflet apex*.—Side leaflets; acute, terminal leaflets; acute to acuminate.

*Leaflet venation*.—Pinnate and slightly reticulate, upper surface 144B in color, lower surface 138B in color.

*Leaflet quantity*.—5, occasionally 7.

*Leaflet margin*.—Up to 7 acute teeth in the middle, sometimes lobed to cleft at the base.

*Leaflet surface*.—Upper surface; glabrous, lower surface; glossy and sparsely covered with short hairs.

*Leaf color*.—Young upper and lower surface; 144A, mature upper surface; 137A, mature lower surface 137D.

*Petioles*.—Up to 8 cm in length, 1.2 mm in diameter, N77A in color, canaliculate in shape, vertical aspect, connate base, surface sparsely hairy; more densely at the node.

*Petiolules*.—Rounded in shape, N77A in color, curling to straight, terminal leaflet up to 3 cm in length, side leaflets up to 1.5 cm in length, 1 mm in diameter.

Inflorescence description:

*Inflorescence type*.—Solitary.

*Inflorescence arrangement*.—Terminal and axillary on young shoots.

*Peduncles*.—Up to 2 mm in length and 3 mm in width, 144C in color, round in shape, surface pubescent, strong.

*Pedicels*.—Up to 9 cm in length, 1 mm in diameter, 144A, tinged N77A in color, round in shape, surface pubescent and sparsely hairy at the base and below the flower, strong with apex nodding.

*Flower buds*.—Nodding, orbicular in shape, acute to acuminate apex, obtuse base, up to 1.5 cm in length and 1.8 cm in diameter, 154B, surface glabrous with villous seams.

*Flower fragrance*.—None.

*Lastingness of the flowers*.—Individual flowers last up to 10 days.

*Flower quantity*.—Average of 3 to 9 per stem.

*Flower type*.—Campanulate.

*Flower aspect*.—Nodding.

*Flower shape*.—Open and bowl-shaped.

*Flower size*.—4 to 5 cm in diameter and 2.5 cm in depth.

*Flower sex*.—Bisexual.

*Receptacle*.—146A in color and 2 mm in diameter.

*Bracts*.—Simple, lanceolate in shape, up to 3 cm in length and 1 cm in width, acute apex, margins are lobed to cleft at the base, cuneate base, venation is reticulate, both surfaces glabrous with main veins on lower surface sparsely hairy and glabrous, color; upper surface 147A, lower surface 147B with veins 144B.

*Tepal number*.—4, occasionally 5 to 6 on terminal flower.

*Tepal shape*.—Lanceolate.

*Tepal aspect*.—Curled.

*Tepal apex*.—Long acuminate.

*Tepal base*.—Cuneate.

*Tepal margin*.—Entire.

*Tepal surface*.—Upper and lower surface glabrous.

*Tepal color*.—Upper surface when opening; 154A, lower surface when opening; 2A with apex 154A, upper surface when fully open; 12A, lower surface when fully open; 12A and changing to 16B as it matures.

*Tepal size.*—Up to 3 cm in length and an average of 1.4 cm in width.

Reproductive organs:

*Gynoecium.*—Average of 100 pistils, up to 1.1 cm in length, ovary; N144C in color and pubescent, style; 145C in color, pubescent, stigma; slightly curled in aspect, N144B in color, pubescent.

*Androecium.*—50 to 100, filaments; up to 7 mm in length, 1 mm in width and linear in shape, surface is sparsely pubescent, N92D in color and 152D at the base, anthers; 3 mm in length, 2 mm in width, linear in shape, and 4D in color, glabrous surface, pollen; 4D in color and low in quantity, connective; elongated, 0.5 mm in length, straight in aspect, apex acute, surface is sparsely pubescent and 137D in color.

*Seed.*—Average of 100, seed head; up to 3.5 cm in diameter, orbicular in shape, seed; 2 mm in length, 1 mm in width, 144A in color, pubescent, seed style; up to 2 cm in length, plumose with silvery hairs, 2D in color near stigma and 144A towards the base, seed stigma; 200A in color and slightly bent.

It is claimed:

1. A new and distinct cultivar of *Clematis* plant named 'Zo14100' as herein illustrated and described.

* * * * *